(12) United States Patent
King et al.

(10) Patent No.: US 9,783,486 B2
(45) Date of Patent: Oct. 10, 2017

(54) PREPARATION OF HIGH MOLECULAR WEIGHT, BRANCHED, ACYCLIC POLYALKYLENEAMINES AND MIXTURES THEREOF

(71) Applicant: Dow Global Technologies LLC, Midland, MI (US)

(72) Inventors: Stephen W. King, League City, TX (US); Sadeka Onam, Midland, MI (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 15/038,984

(22) PCT Filed: Nov. 24, 2014

(86) PCT No.: PCT/US2014/067081
§ 371 (c)(1),
(2) Date: May 24, 2016

(87) PCT Pub. No.: WO2015/084619
PCT Pub. Date: Jun. 11, 2015

(65) Prior Publication Data
US 2016/0376221 A1    Dec. 29, 2016

Related U.S. Application Data

(60) Provisional application No. 61/910,535, filed on Dec. 2, 2013.

(51) Int. Cl.
| C07C 211/14 | (2006.01) |
| C07C 209/02 | (2006.01) |
| C08G 73/02 | (2006.01) |
| C07C 209/64 | (2006.01) |
| B01J 23/889 | (2006.01) |

(52) U.S. Cl.
CPC ......... *C07C 211/14* (2013.01); *B01J 23/8896* (2013.01); *C07C 209/02* (2013.01); *C07C 209/64* (2013.01); *C08G 73/0206* (2013.01); *C08G 73/0213* (2013.01)

(58) Field of Classification Search
CPC ... C07C 211/14; C07C 209/02; C07C 209/64; C08G 73/0206; C08G 73/0213; B01J 23/8896
See application file for complete search history.

(56) References Cited

U.S. PATENT DOCUMENTS

| 2,861,995 A | 11/1958 | MacKenzie |
| 3,110,732 A | 11/1963 | Speranza et al. |
| 3,394,186 A | 7/1968 | Muhlbauer |
| 3,658,692 A | 4/1972 | Gilbert et al. |
| 3,733,325 A | 5/1973 | Yeakey |
| 3,847,754 A | 11/1974 | Oliver |
| 4,032,411 A | 6/1977 | Tornquist et al. |
| 4,073,750 A | 2/1978 | Yates et al. |
| 4,111,840 A | 9/1978 | Best |
| 4,123,462 A | 10/1978 | Best |
| 4,209,424 A | 6/1980 | Le Goff et al. |
| 4,264,776 A | 4/1981 | Hershman et al. |
| 4,328,370 A | 5/1982 | Fazio |
| 4,400,539 A | 8/1983 | Gibson et al. |
| 4,404,405 A | 9/1983 | Winters |
| 4,510,263 A | 4/1985 | Pereira et al. |
| 4,552,961 A | 11/1985 | Herdle |
| 4,568,746 A | 2/1986 | Cowherd, III |

(Continued)

FOREIGN PATENT DOCUMENTS

| EP | 0075940 B1 | 9/1985 |
| EP | 0163253 A2 | 12/1985 |
| EP | 0197611 A2 | 10/1986 |
| EP | 0197612 A2 | 10/1986 |

(Continued)

OTHER PUBLICATIONS

Reichle, Walter T., "Reactions of Aliphatic Diamines in H+-Pentasils," Journal of Catalysis 144, pp. 556-568, Jun. 3, 1993.

(Continued)

*Primary Examiner* — Paul A Zucker
*Assistant Examiner* — Mark Luderer
(74) *Attorney, Agent, or Firm* — Kagan Binder, PLLC (57) ABSTRACT

A process for preparing high molecular weight, branched, acyclic polyalkyleneamines comprising transaminating a reaction mixture that includes at least a first polyalkyleneamine component that contains at least two non-tertiary amine groups separated from one another by a ternary or higher carbon atom and a second polyalkyleneamine component having the formula wherein x, y, and z are the same or different and are integers of from 1 to 10; a, b, c, d, e, and f are the same or different and are H or hydrocarbyl of from 1 to 10 carbon atoms; A, B, C, D, E, are the same or different and are H or hydrocarbyl of from 1 to 10 carbon atoms; provided that at least two of the amine groups are primary or secondary.

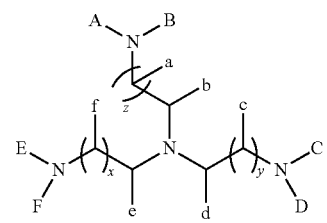

15 Claims, 3 Drawing Sheets

(56) References Cited

U.S. PATENT DOCUMENTS

| | | |
|---|---|---|
| 4,584,405 A | 4/1986 | Vanderpool |
| 4,602,091 A | 7/1986 | Brennan |
| 4,698,427 A | 10/1987 | Vanderpool |
| 4,708,945 A | 11/1987 | Murrell et al. |
| 4,729,981 A | 3/1988 | Kobylinski et al. |
| 4,801,573 A | 1/1989 | Eri et al. |
| 4,806,517 A | 2/1989 | Vanderpool et al. |
| 4,845,296 A | 7/1989 | Ahmed et al. |
| 4,870,044 A | 9/1989 | Kukes et al. |
| 4,883,826 A | 11/1989 | Marugg et al. |
| 4,888,316 A | 12/1989 | Gardner et al. |
| 4,906,782 A | 3/1990 | Hara et al. |
| 4,914,072 A | 4/1990 | Grice et al. |
| 4,922,024 A | 5/1990 | Bowman et al. |
| 4,927,931 A | 5/1990 | Molzahn et al. |
| 4,983,735 A | 1/1991 | Hartwell et al. |
| 5,030,740 A | 7/1991 | Bowman et al. |
| 5,073,635 A | 12/1991 | Bowman et al. |
| 5,120,815 A | 6/1992 | Marugg et al. |
| 5,166,442 A | 11/1992 | Hartwell et al. |
| 5,210,306 A | 5/1993 | Doumaux, Jr. et al. |
| 5,214,215 A | 5/1993 | King et al. |
| 5,222,599 A | 6/1993 | Boyce |
| 5,225,600 A | 7/1993 | King et al. |
| 5,248,827 A | 9/1993 | Hara et al. |
| 5,256,786 A | 10/1993 | Bowman et al. |
| 5,288,909 A | 2/1994 | Hartwell et al. |
| 5,321,160 A | 6/1994 | Hironaka et al. |
| 5,352,835 A | 10/1994 | Dai et al. |
| 5,362,700 A | 11/1994 | Doumaux, Jr. |
| 5,362,914 A | 11/1994 | Su |
| 5,410,086 A | 4/1995 | Burgess |
| 5,410,087 A | 4/1995 | Hartwell et al. |
| H1447 H | 6/1995 | Linton |
| 5,455,352 A | 10/1995 | Huellmann et al. |
| 5,552,363 A | 9/1996 | Pannell et al. |
| 5,554,793 A | 9/1996 | Hartwell et al. |
| 5,567,847 A | 10/1996 | Vedage et al. |
| 5,721,305 A | 2/1998 | Eshuis et al. |
| 5,750,790 A | 5/1998 | King |
| 5,817,593 A | 10/1998 | Chang et al. |
| 5,851,948 A | 12/1998 | Chuang et al. |
| 5,935,889 A | 8/1999 | Murrell et al. |
| 5,994,585 A | 11/1999 | Gunther-Hanssen |
| 6,117,814 A | 9/2000 | Plecha et al. |
| 6,124,367 A | 9/2000 | Plecha et al. |
| 6,169,207 B1 | 1/2001 | Tsuneki et al. |
| 6,222,008 B1 | 4/2001 | Gelles |
| 6,235,677 B1 | 5/2001 | Manzer et al. |
| 6,306,795 B1 | 10/2001 | Ryan et al. |
| 6,465,530 B2 | 10/2002 | Roy-Auberger et al. |
| 6,465,601 B1 | 10/2002 | Wiesendanger et al. |
| 6,469,214 B2 | 10/2002 | Melder et al. |
| 6,534,441 B1 | 3/2003 | Bartley et al. |
| 6,576,796 B1 | 6/2003 | Funke et al. |
| 6,703,343 B2 | 3/2004 | Park |
| 6,977,273 B2 | 12/2005 | Roy-Auberger et al. |
| 7,045,485 B2 | 5/2006 | Kelkar et al. |
| 7,053,246 B2 | 5/2006 | Gerlach et al. |
| 7,053,247 B2 | 5/2006 | Lif et al. |
| 7,056,857 B2 | 6/2006 | Srinivasan et al. |
| 7,067,455 B2 | 6/2006 | Chen et al. |
| 7,256,154 B2 | 8/2007 | Moon et al. |
| 7,323,100 B2 | 1/2008 | Espinoza et al. |
| 7,342,976 B2 | 3/2008 | McCallister |
| 7,348,293 B2 | 3/2008 | Timken |
| 7,393,978 B2 | 7/2008 | Frauenkron et al. |
| 7,541,310 B2 | 6/2009 | Espinoza et al. |
| 7,595,276 B2 | 9/2009 | Kodama et al. |
| 7,727,931 B2 | 6/2010 | Brey et al. |
| 7,745,369 B2 | 6/2010 | Bhan et al. |
| 7,824,656 B2 | 11/2010 | Idem et al. |
| 7,981,836 B2 | 7/2011 | Kanazirev et al. |
| 7,989,384 B2 | 8/2011 | Brey et al. |
| 8,187,197 B2 | 5/2012 | Shapira et al. |
| 8,188,318 B2 * | 5/2012 | Petraitis ............ C07C 209/08 564/470 |
| 8,293,676 B2 | 10/2012 | King et al. |
| 8,314,048 B2 | 11/2012 | Brey et al. |
| 8,492,592 B2 | 7/2013 | King et al. |
| 9,000,217 B2 | 4/2015 | King |
| 2003/0013873 A1 | 1/2003 | Neumann et al. |
| 2004/0171884 A1 | 9/2004 | Lif et al. |
| 2005/0095189 A1 | 5/2005 | Brey et al. |
| 2006/0030726 A1 | 2/2006 | Telschow |
| 2006/0276649 A1 | 12/2006 | Frauenkron et al. |
| 2007/0100144 A1 | 5/2007 | Frauenkron et al. |
| 2008/0003131 A1 | 1/2008 | Bauer et al. |
| 2008/0132725 A1 | 6/2008 | Melder et al. |
| 2008/0275352 A1 | 11/2008 | Shapira et al. |
| 2009/0018040 A1 | 1/2009 | Eveland et al. |
| 2010/0056366 A1 | 3/2010 | Lee |
| 2010/0087681 A1 | 4/2010 | Petraitis et al. |
| 2010/0087682 A1 | 4/2010 | King et al. |
| 2010/0087683 A1 | 4/2010 | Cook et al. |
| 2010/0087684 A1 | 4/2010 | Do et al. |
| 2010/0087685 A1 | 4/2010 | King et al. |
| 2010/0094007 A1 | 4/2010 | King et al. |
| 2010/0094008 A1 | 4/2010 | King et al. |
| 2010/0121064 A1 | 5/2010 | Dahmen et al. |
| 2010/0137642 A1 | 6/2010 | King et al. |
| 2010/0197481 A1 | 8/2010 | Brey et al. |
| 2011/0015439 A1 | 1/2011 | Hanson et al. |
| 2011/0280780 A1 | 11/2011 | Brey et al. |
| 2012/0238780 A1 | 9/2012 | King et al. |
| 2012/0277435 A1 | 11/2012 | King et al. |
| 2013/0023698 A1 | 1/2013 | King et al. |
| 2013/0225864 A1 | 8/2013 | King |

FOREIGN PATENT DOCUMENTS

| | | |
|---|---|---|
| EP | 0212287 A2 | 3/1987 |
| EP | 0284398 A2 | 9/1988 |
| EP | 0308894 B1 | 12/1991 |
| EP | 0254335 B1 | 1/1992 |
| EP | 0526851 B1 | 2/1993 |
| EP | 0308893 B1 | 1/1994 |
| EP | 737669 B1 | 10/1996 |
| EP | 1211238 B1 | 6/2002 |
| EP | 1249440 A1 | 10/2002 |
| GB | 1508460 A | 5/1978 |
| GB | 1551127 A | 8/1979 |
| IL | 57019 A | 9/1983 |
| JP | 60-239442 A | 11/1985 |
| JP | 60-239443 A | 11/1985 |
| JP | 05097777 A | 4/1993 |
| RU | 2186761 C1 | 8/2002 |
| RU | 2226188 C1 | 3/2004 |
| RU | 2226189 C1 | 3/2004 |
| WO | 9217437 A1 | 10/1992 |
| WO | 99/24389 A1 | 5/1999 |
| WO | 01/44150 A2 | 6/2001 |
| WO | 01/66247 A2 | 9/2001 |
| WO | 01/98243 A1 | 12/2001 |
| WO | 03/010125 A1 | 2/2003 |
| WO | 2005/012223 A1 | 2/2005 |
| WO | 2005/014523 A1 | 2/2005 |
| WO | 2005/061430 A1 | 7/2005 |
| WO | 2006/053342 A2 | 5/2006 |
| WO | 2006/060206 A1 | 6/2006 |
| WO | 2006/114417 A2 | 11/2006 |
| WO | 2007/093514 A1 | 8/2007 |
| WO | 2008/104582 A2 | 9/2008 |
| WO | 2009/083580 A1 | 7/2009 |
| WO | 2010/042159 A1 | 4/2010 |
| WO | 2012/064483 A1 | 5/2012 |
| WO | 2012/064484 A1 | 5/2012 |

OTHER PUBLICATIONS

Zagidullin, R.N., Abstract, "Simultaneous manufacture of acyclic and cyclic di- and polyethylenepolyamines", pp. 267-269, 1987.

(56) References Cited

OTHER PUBLICATIONS

Komiyama et al., "Concentration Profiles in Impregnation of Porous Catalysts: Nickel on Alumina," Journal of Catalysis, vol. 63, School of Chemical Engineering, Cornell University, and Chevron Research Company, pp. 35-52 (1979).

Lewi, Abstract, Database Beilstein (online), Beilstein Institute for Organic Chemistry, Doklady Akademii Nauk SSSR, vol. 78, pp. 725-727 (1951).

Tanabe et al., "A New Hypothesis Regarding the Surface Acidity of Binary Metal Oxides," Bulletin of the Chemical Society of Japan, vol. 47(5), Department of Chemistry, Faculty of Science, Hokkaido University, pp. 1064-1066 (1974).

Abstract, Kiebach et al., "Solvothermal synthesis of [C6H17N3]Sb10S16: A new thioantimonate(III) with an in-situ formed organic amine cation" (2005).

Olson, "Thermodynamics of hydrogen-bonding mixtures 4: Ge, He, Se and CEP and possible double azeotropy of water + N-methylethylenediamine," Fluid Phase Equilibria 185 (2001) pp. 209-218.

Zhao Fenwei et al, Study Process on Reduction Amination Catalyst in the Synthesis of Ethylenediamine, Chemical Production and Technology, vol. 14, No. 6, pp. 38-41, (2007).

Zhang et al., "Amination of Ethanolamine Over Cobalt Modified H-ZSM-5 Catalysts" Catalysis Communications 8, pp. 1102-1106, (2007).

Zagidullin, et al., Removal of dichloroethane from waste gases of chlorinated organic compound production, Khimicheskaya Promyshlennost, (2), 82-84 (1991 ).

Pine Organic Chemistry [I], 1994, 8th issue, p. 326-327 in Japanese.

\* cited by examiner

PREPARATION OF HIGH MOLECULAR WEIGHT, BRANCHED, ACYCLIC POLYALKYLENEAMINES AND MIXTURES THEREOF

PRIORITY CLAIM

The present patent application claims priority to International Application No. PCT/US2014/067081, filed Nov. 24, 2014, which in turn claims priority to U.S. Provisional patent application Ser. No. 61/910,535 filed on Dec. 2, 2013, and entitled "PREPARATION OF HIGH MOLECULAR WEIGHT, BRANCHED, ACYCLIC POLYALKYLENEAMINES AND MIXTURES THEREOF," wherein the disclosures of these applications are incorporated herein by reference in their respective entireties for all purposes.

The present invention relates to the preparation of high molecular weight, branched, acyclic polyalkyleneamines (e.g., compounds containing 4 or more N atoms). Preferably the present invention relates to the preparation of high molecular weight, branched, acyclic polyalkyleneamines containing at least 5 N atoms. The molar ratio of the starting compounds can be adjusted to customize the product composition for desired end uses.

BACKGROUND OF THE INVENTION

High molecular weight polyalkyleneamines have found use in many applications. For example, they have been used to make ashless oil dispersants for lubricating oil additives, and as asphalt additives. High molecular weight polyalkyleneamines have also been derivatized to make polyamides, which in turn are useful as epoxy curing agents.

The most widely practiced commercial process for the production of high molecular weight polyalkyleneamines is based on the reaction of ethylene dichloride (EDC) with ammonia ($NH_3$) followed by neutralization with sodium hydroxide (NaOH) to produce polyethyleneamines and salt. This process is sometimes referred to as the "EDC Process".

Another family of high molecular weight polyalkyleneamines includes polyethyleneimines (PEI), which are produced by an acid-catalyzed ring opening homopolymerization of ethyleneimine (or aziridine). These materials can range in molecular weight from 800-750,000 and comprise a combination of primary, secondary, and tertiary amino groups, typically in a molar ratio of approximately 1:2:1 with a branching site every 3-3.5 nitrogen atoms along any given chain segment. Depending on the reaction conditions different degrees of branching can be achieved.

Other publications that disclose the preparation of high molecular weight polyalkyleneamines include U.S. Patent Publication 2009/0018040, which discloses a method in which lower molecular weight ethyleneamines are coupled through the use of difunctional linking groups such as epihalohydrins, maleates, α-halogenated acids, and malonates.

Another method for making polyalkyleneamines involves the transamination of lower molecular weight polyalkyleneamines. See for example, GB Patent No. 1508460 and U.S. Pat. Nos. 4,568,746 and 7,053,247, which each discloses the transamination of ethylenediamine (EDA). See also GB Patent No. 1551127 which discloses the transamination of 1,3-diaminopropane (1,3-DAP); U.S. Pat. No. 6,465,601 which discloses the preparation of mixed amines by the transamination of a substituted phenolic compound (Mannich base) with another amine; US 2008/0132725 A1 which discloses the preparation of bis(3-aminopropyl)amine [dipropylenetriamine (DPTA)] by the continuous reaction of 1,3-propylenediamine in the presence of a heterogeneous catalyst in a reaction column; WO 2010042159 which discloses the manufacture of cyclic triamines by the transamination of tris(2-aminoethyl)amine (TAEA) to produce 2-(piperazin-1-yl)ethanamine (AEP); and United States Published Patent Application 2013-0225864 A1 which discloses the manufacture of high molecular weight predominantly linear acyclic, non-branched amines.

These methods tend to produce product mixtures whose contents promote either the formation of cyclic polyalkyleneamines or linear non-branched polyalkyleneamines and discourage the formation of higher molecular weight, branched, acyclic polyalkyleneamines. As a result there remains a need for a method to better control the product mix for making high molecular weight, branched acyclic, polyalkyleneamines.

While cyclic and linear non-branched species are desired for some applications, higher molecular weight, branched, acyclic species are also desired for many other applications. For example, they are useful in paper manufacture, water treatment conditioning, as plating bath agents, as dispersing agents, as asphalt additives, as corrosion inhibitors, as epoxy curing agents, as fuel and lubricant additives, as mineral processing aids, in wood treating, etc. Other exemplary uses for product mixtures of the invention include other polymer curing, hydrocarbon purification, surface activation, in fabric softeners, as textile additives, and as surfactants.

Applicants have discovered an efficient and effective methodology for producing high molecular weight, branched acyclic polyalkyleneamines that are substantially free of cyclic amine species.

SUMMARY OF THE INVENTION

The present invention provides strategies for using transamination to prepare high molecular weight, branched, acyclic polyalkyleneamines and product mixtures containing such polyalkyleneamines. The polyalkyleneamines and product mixtures of the invention are substantially free of cyclic amines. Adjusting the feed mole ratio of the reactants can easily modify the degree of branching. Additionally, the polyalkyleneamines and product mixtures of the invention are preferably liquids across a broader molecular weight range than are the corresponding linear amines, and in some cases can moderate the rate of reaction of the amine compared to linear amines containing the same number of N atoms.

The present invention is based in part upon using reaction mixtures for transamination that include a first component that comprises at least a first linear, acyclic polyalkyleneamine, and a second acyclic, branched, polyalkyleneamine, which reaction mixture can be transaminated to form the desired product or product mixture while minimizing the formation of cyclic polyalkyleneamines.

One embodiment of the invention provides a method of making a high molecular weight, branched, substantially acyclic polyalkyleneamine-containing product comprising the steps of:
(a) providing a reaction composition comprising a first linear polyalkyleneamine that has at least two non-tertiary amine groups separated by at least a ternary carbon atom spacing and at least one second polyalkyleneamine having the formula (I)

(I)

wherein x, y, and z are the same or different and have values of from 1 to 10;

a, b, c, d, e, and f are the same or different and are H or hydrocarbyl of from 1 to 10 carbon atoms; A, B, C, D, E, are the same or different and are H or hydrocarbyl of from 1 to 10 carbon atoms; provided that at least two of the amine groups are primary or secondary; and (b) subjecting the reaction composition to a transamination reaction in the presence of a hydrogenation/dehydrogenation catalyst to obtain the linear high molecular weight, branched, acyclic polyalkyleneamine-containing mixture.

In yet another embodiment the second polyalkyleneamine is selected from tris(2-aminoethyl)amine (TAEA), tris(2-aminopropyl)amine, and tris(3-aminopropyl)amine. Preferably the second polyalkyleneamine is TAEA.

In a further embodiment of the invention the reaction mixture can undergo transamination to produce a variety of branched products. By changing the molar ratio of first and second polyalkyleneamines, a wide range mixture of branched materials can be produced while minimizing the formation of cyclic materials. The process is capable of generating a product mixture having a high concentration of high molecular weight branched, acyclic polyalkyleneamines (≥N4) that are liquids at ambient temperature.

In another aspect, the present invention relates to a method of making a high molecular weight mixture of polyalkyleneamine congeners comprising the steps of combining first and second nitrogen-containing components as described above and subjecting the first and second nitrogen-containing components to a transamination reaction in the presence of a hydrogenation/dehydrogenation catalyst to obtain a product or a product mixture comprising the mixture of polyalkyleneamine congeners. It will be recognized by those skilled in the art that high molecular weight polyalkyleneamines containing 4 or more nitrogens can have complex mixtures containing the same number of nitrogens. These mixtures are often called congeners. As used herein, congeners of polyalkyleneamine products are variants, or different configurations of the polyalkyleneamine product(s), that contain the same number of N atoms.

In another aspect, the present invention relates to a method of making an amine mixture, comprising the steps of: providing a reaction mixture comprising a first and second polyalkyleneamine as described above, wherein the molar content of the first polyalkyleneamine comprises at least about 60-99%, preferably 75-97%, most preferably 80-95% of the reaction mixture; and subjecting the reaction mixture to a transamination reaction in the presence of a hydrogenation/dehydrogenation catalyst.

In another aspect, the present invention relates to a mixture of polyalkyleneamines obtained by the method(s) of the invention.

As used herein, the term polyalkyleneamine refers to a compound that includes at least two amine groups.

As used herein, the term high molecular weight refers to the molecular weight of a polyalkyleneamine product(s) resulting from the practice of the present invention. These polyalkyleneamines typically comprise 4 or more N atoms, preferably at least 5 N atoms. Thus, high molecular weight includes a number average molecular weight of at least about 203. The upper limit of the number average molecular weight is not critical to the invention. In an aspect of the invention, the upper limit of the number average molecular weight is about 1000, preferably about 800.

As used herein, the term substantially free of cyclic amine species means that the polyalkyleneamine or polyalkyleneamine product mixture contains no more than about 25 weight percent, of a cyclic polyalkyleneamine.

In contrast to the polyalkyleneamine reactants, the polyalkyleneamine products made using methods of the present invention may include two or more primary, secondary, and/or tertiary amine groups, or combinations thereof. Preferred polyalkyleneamine reactants are primary diamines. Preferably the reactants contain less tertiary amine than primary and secondary amine. The nature of the product composition can be readily customized for desired end uses simply by adjusting the molar ratio of the amine reactants in the reaction mixture.

The practice of the invention can be used to prepare compositions containing novel branched congener products of pentamines, or higher polyalkyleneamines. The methodology of the invention provides much better control over the production of predominately high molecular weight, branched, acyclic polyalkyleneamines and mixtures thereof, useful for a variety of end-use applications.

DETAILED DESCRIPTION OF PRESENTLY PREFERRED EMBODIMENTS

Reference will now be made in detail to representative embodiments of the invention. While the invention will be described in conjunction with the enumerated embodiments, it will be understood that they are not intended to limit the invention to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods, materials, and compositions described.

All publications and patents mentioned herein are incorporated herein by reference in their respective entireties for the purpose of describing and disclosing, for example, the constructs and methodologies that are described in the publications which might be used in connection with the presently described invention.

Unless defined otherwise herein, technical and scientific terms used have the same meaning as commonly understood by one of ordinary skill in the art to which this invention belongs. Although any methods, devices, and materials similar or equivalent to those described herein can be used in the practice or testing of the invention, the preferred methods, devices and materials are now described.

The present invention provides strategies for making high molecular weight, branched, predominately acyclic polyalkyleneamine mixtures by methodologies that comprise subjecting a first amine component and a second amine component to a transamination reaction to produce the desired high molecular weight amine product or product mixture.

Examples of first components useful in the invention include 1,3-diaminopropane (1,3-DAP); 1,3-butanediamine; 1,3-pentanediamine; 2,2-dimethyl-1,3-propanediamine; 2,2-diethyl-1,3-propanediamine; 1,3-diamino-2-phenylpropane; 2-(aminomethyl)-2-methyl-1,3-propanediamine; combinations of these, and the like. Without limiting the scope of the present invention, generally having the first component free of any branching leads to higher reactivity with the second amine thusly minimizing the amount of cyclic material made. Thusly, 1,3-DAP; 1,3-butanediamine; and 1,3-pentanediamine are preferred. 1,3-DAP is most preferred. The first nitrogen-containing reactant preferably has at least two non-tertiary amine groups, separated from one another by a ternary or greater carbon group.

In an aspect of the invention, the second polyalkyleneamine component comprises the compound of formula (I) as set out above. In formula (I), at least two of the amine groups are non-tertiary amine groups. That is, at least two of the amine groups are primary and/or secondary amine groups. The amine groups of the compound of formula (I) are separated from one another by either binary or greater atom spacing. The compound of formula (I) is preferably TAEA.

In preferred reaction mixture embodiments, the first polyalkyleneamine component includes at least 1,3 diaminopropane (DAP) and any other second polyalkyleneamine component as discussed above.

Transamination of the reactant mixture results in a product mixture that comprises the high molecular weight, branched, acyclic polyalkyleneamine products that are tetra, or higher in functionality with respect to amine and generally include binary and greater than binary spacing between the amine groups.

Advantageously, transamination of mixtures of the amine components provides a significant quantity of the amine products of the invention in the product mixture. They may also include some minor amounts (i.e., less than about 25 weight percent (preferably less than 1 weight %) of cyclic components.

By changing the molar content of the reactant mixture as described above, product mixtures with a customized composition suiting a desired end use may be obtained. Thus, information can be obtained that is indicative of the product composition that results, desirably for a given set of transamination conditions, as a function of the molar content of the reactant(s) over a suitable molar content. Using this information, transamination can be practiced using a molar content effective to provide a desired product composition. Molar content can be selected that favors the formation of various predominately acyclic polyalkyleneamine congener products.

Adjustment of other reaction conditions also helps customize the product mixture. Examples of other reaction conditions that can be used to customize product compositions include the nature of the catalyst, the concentration of catalyst on its carrier in the case of heterogeneous catalysts, the physical form of the catalyst, the pressure of the reaction, the concentration of $H_2$ during the reaction, the amine flow rate, conversion, temperature, combinations of these, and/or the like.

The product mixture resulting from transamination can be used as is, packaged stored, or modified as desired depending upon the desired end use. In one mode of practice, the product mixture may include amine products with a range of volatilities. If a limited VOC specification is applicable, more volatile components can be removed before the remainder is used, stored, or otherwise handled. If a limited viscosity specification is applicable, more viscous components can be obtained by refining the more volatile (less viscous) components before the remainder is used, stored, or otherwise handled. Components that are removed, and even some by-products, have commercial value and may have many uses. These include being recycled as a feed for the transamination reaction, refined to recover some of the product(s) in more pure form, used as reactants in other reactions, used as is or with any desired modification as products such as epoxy curing agents, combinations of these, and the like. Different components of the product mixture may have different uses, and so the product mixture can be separated into these components based upon the desired end use.

Transamination may be carried out in a variety of ways. In accordance with a preferred mode of practice, the reactants are combined and caused to react in a suitable reactor volume in the presence of a suitable catalyst under temperature and pressure conditions effective to cause the transamination reaction.

The methods of the invention can be practiced in any suitable reactor. These include batch reactors, continuous fixed bed reactors, slurry bed reactors, fluidized bed reactors, catalytic distillation reactors, combinations of these, and the like.

A variety of catalysts can be used in the practice of the present invention. Catalysts can be acidic, alkaline, neutral, or a combination of different catalysts can be used. Representative classes of catalysts include metals, alloys, intermetallic compositions, or molecules (such as oxides, nitrides, phosphates, silicates, and the like), or mixtures of one or more transition metals, including the lanthanoid and/or actinoid series. A wide variety of catalysts applicable to amine chemistry are described in U.S. Pat. Nos. 6,534,441; 5,256,786; 5,073,635; 4,983,735; 5,030,740; 4,927,931; 5,222,599; 4,906,782; 4,922,024; 4,806,517; 4,584,405; 4,552,961; 5,455,352; 5,248,827; 4,602,091. See also Russian patents 2226188 and 2186761.

In a preferred embodiment, the catalyst incorporates one or more hydrogenation and/or dehydrogenation catalysts. Hydrogenation generally refers to a chemical reaction involving the addition of hydrogen, and the process is often used to reduce or saturate organic materials. The reverse reaction in which hydrogen is removed from an organic molecule is referred to as dehydrogenation. The use of hydrogenation and/or dehydrogenation catalysts has been found to be useful for transamination.

A wide variety of hydrogenation/dehydrogenation catalysts are known. Platinum group metals, particularly platinum, palladium, rhodium, and ruthenium form highly active hydrogenation/dehydrogenation catalysts. These are known to operate at lower temperatures and lower pressures of $H_2$. Non-precious metal catalysts, especially those based on nickel (such as Raney nickel and Urushibara nickel) have also been developed as economical alternatives. Other hydrogenation/dehydrogenaton catalysts might incorporate iron, copper, chromium, molybdenum, cobalt, osmium, iridium, rhenium and/or the like.

In particularly preferred embodiments, the catalyst material incorporates hydrogenation/dehydrogenation catalytic ingredients comprising nickel and rhenium. The weight ratio of nickel to rhenium may vary over a wide range. For instance, the weight ratio of nickel to rhenium may be in the range from about 1:1000 to 1000:1, preferably 1:100 to 100:1, more preferably 1:50 to 50:1. Even more desirably, the weight ratio of nickel to rhenium is within these ranges with the proviso that the weight ratio is also greater than 1:1. In illustrative embodiments, using a weight ratio from about 3:1 to 10:1 would be suitable. In preferred embodiments in which a heterogeneous catalyst incorporates nickel and rhenium, a useful group of supports include alumina-silicate particles. Such catalysts and methods of making such heterogeneous catalysts on such supports are further described in U.S. Pat. No. 6,534,441. Such catalysts are also further described in U.S. Pat. Nos. 8,293,676; 8,187,197; and 8,492,592.

The catalysts can be heterogeneous, homogeneous, or a combination thereof. Homogeneous catalysts are soluble in the reaction medium. Illustrative homogeneous catalysts include the rhodium-based compound known as Wilkinson's catalyst and the iridium-based Crabtree's catalyst. Heterogeneous catalysts are solids that are insoluble in contact with the reaction medium, which may be in liquid, gas or other fluid form.

Heterogeneous catalysts are preferred. Often, heterogeneous catalysts comprise one or more catalytic materials supported upon a suitable substrate. The substrate may be used in various shapes or combinations such as, for example, powder, particle, pellet, granule, extrudate, fiber, shell, honeycomb, plate, or the like. The particles can be regular in shape, irregular, dendritic, dendrite-free, or the like. Preferred supports are particulate in nature or powders.

Particulate support may have a so-called guest/host structure, which may be prepared by adsorbing or adhering fine (less than 100 micrometers, preferably less than 50 micrometers and most preferably less than 10 micrometer in size) nanoporous particles on coarser (greater than 30 mesh) particles. The smaller particles are referred to as guests, while the large particles supporting them are referred to as hosts. This small-particle-supported-on-a-larger-particle composite structure provides very high total exterior surface area while retaining the desirable gas passing characteristics, i.e., low pressure drop, of a coarser particle. In addition, by using smaller particles in constructing these composite particles, inexpensive, coarser particles can be used. Thus, very inexpensive, highly active catalyst particles can be prepared since the bulk of the volume of a catalyst bed may be taken up by the inexpensive, underlying, coarser particles.

The catalyst material can be incorporated into or onto a suitable support. A wide variety of materials may serve as suitable supports in the practice of the present invention. Representative examples include carbonaceous materials, silicaceous materials (such as silica), metal compounds such as metal oxides, combinations of these, and the like. Representative metal oxides include oxides of one or more of magnesium, aluminum, titanium, vanadium, chromium, manganese, iron, cobalt, nickel, copper, zinc, gallium, germanium, strontium, yttrium, zirconium, niobium, molybdenum, technetium, ruthenium, rhodium, palladium, silver, cadmium, indium, iron, tin, antimony, barium, lanthanum, hafnium, thallium, tungsten, rhenium, osmium, iridium, and platinum.

Examples of carbonaceous substances include activated carbon and graphite. Suitable activated carbon particles may be derived from a wide variety of source(s) including coal, coconut, peat, any activated carbon(s) from any source(s), combinations of at least two of these, and/or the like.

Preferably the support comprises guest and/or host particles. Often, the catalyst material is incorporated mainly onto the guest material before or after the guest/host composite is formed. Guest/host structures and methods of making these are further described in U.S. Pat. Nos. 7,727,931; 7,989,384; and 8,314,048.

The support particles can comprise an acidic mixed metal oxide that includes a transitional alumina and a second metal oxide. The transitional alumina can comprise delta or theta alumina, alone or in combination with another transitional phase, an alpha alumina, and/or gamma alumina. The second metal oxide has a weight percentage that is less than the weight percentage of alumina. In some aspects, the support portion comprises at least 50 weight percent transitional phase alumina.

The catalyst portion is typically 25 weight percent or less of the catalyst composition, and preferably comprises nickel in an amount in the range of 2 to 20 weight percent, more preferably in the range of 5 to 10 weight percent, based upon total catalyst composition weight.

The second metal oxide can comprise at least one element selected from Group IIA, IIIA, IVA, VA, VIA, IIB, IIIB, IVB, VB, VIB, VIIB or a rare earth element of the Periodic Table. In some embodiments, the second metal oxide is selected from silicon, lanthanum, magnesium, zirconium, boron, titanium, niobium, tungsten and cerium. In some illustrative embodiments, the second metal oxide comprises silicon.

In some aspects, the support portion can comprise at least 50 weight percent transitional alumina, or at least 90 weight percent transitional alumina. When present, alpha alumina and/or gamma alumina can be included in an amount less than 50 weight, based upon the weight of the alumina support portion. The amount of the various phases of alumina can be selected to provide a support portion having a desired surface area, such as in the range of about 10 $m^2/g$ to about 200 $m^2/g$. In some aspects, the second metal oxide can be present in the support portion in an amount in the range of 5 weight percent to 50 weight percent, based upon the weight of the support portion. In illustrative embodiments, the support portion comprises the second metal oxide in an amount in the range of 5 weight percent to 35 weight percent, based upon the weight of the support portion.

The support portion of the catalyst composition can be provided with a desired surface area. In some embodiments, the support portion has a surface area in the range of about 10 $m^2/g$ to about 200 $m^2/g$, or in the range of about 40 $m^2/g$ to about 180 $m^2/g$, or in the range of about 80 $m^2/g$ to about 180 $m^2/g$. Further, the support portion can be provided with a morphology that minimizes as much as possible mass transfer resistance. In some embodiments, the catalyst composition can be provided with a morphology that reduces or minimizes mass transfer resistance.

Optionally, the catalyst composition can further comprise one or more selectivity promoters to enhance selectivity of the catalyst composition. The promoter may be a metal (or oxide) which when incorporated into the catalyst composition further enhances the productivity and/or selectivity in the amination reaction. As an example, metals or metal oxides for use as promoters are compounds containing elements selected from Group IA, Group IIA, Group IIIA Group IVA, Group VA, Group VIA, Group VIIA, Group VIIIA, Group IB, Group IIB and Group IVB of the Periodic Table (IUPAC format). Exemplary metals include, for example, copper, cobalt, chromium, rhodium, iridium, ruthenium, rhenium, zinc, palladium, platinum, sodium, calcium, magnesium, strontium, lithium, potassium, barium, cesium, lanthanum, tungsten, iron, silver, titanium, manganese, niobium, aluminum, tin and mixtures of these metals. Some particularly useful metals include magnesium, zinc, niobium, chromium, ruthenium, cobalt, copper, tin and mixtures thereof.

An exemplary catalyst composition can comprise (i) a first metal oxide selected from one or more of iron, cobalt, nickel, copper, ruthenium, rhodium, palladium, and platinum, and (ii) optionally at least one other metal oxide selected from magnesium, aluminum, titanium, vanadium, boron, chromium, manganese, zinc, gallium, germanium, strontium, yttrium, zirconium, niobium, molybdenum, technetium, palladium, silver, cadmium, indium, iron, tin, antimony, barium, lanthanum, hafnium, thallium, tungsten, rhenium, osmium, and iridium.

Preferred catalyst compositions comprise nickel and rhenium as catalytic metals. In some aspects, the nickel and rhenium are present in the catalyst portion in a weight ratio in the range of 3:1 to 15:1. The selectivity promoter can be present at a promoter/nickel weight ratio of 0.1 to 0.5 in such catalyst compositions.

Preferred catalyst compositions include those prepared by incorporating at least two catalytically effective transamination metals (nickel and rhenium) on an acidic mixed metal oxide support. The acidic mixed metal oxide support comprises transitional alumina (aluminum oxide ($Al_2O_3$)). Such transamination catalyst compositions can provide a higher ratio of linear (acyclic) to cyclic products when compared to similar catalysts that do not contain a transitional alumina-based acidic mixed metal oxide support.

In some preparations of the catalyst composition, the catalyst portion includes a mixture of nickel and rhenium in the composition in a predetermined weight ratio. In some cases, the weight ratio of the nickel and rhenium in the composition is in the range of about 3:1 to about 15:1. In some aspects, nickel is present in an amount in the range of about 2 weight percent to about 20 weight percent, and rhenium is present in the composition in the range of about 0.5 weight percent to about 7 weight percent. In some aspects, nickel is present in an amount in the range of about 5 weight percent to about 8.5 weight percent, and rhenium is present in the composition in the range of about 1 weight percent to about 2.5 weight percent. An exemplary catalyst portion includes nickel at about 6.8 weight percent and rhenium at about 1.8 weight percent.

Promoters can be added to the catalyst composition either by co-impregnation with nickel and rhenium or they can be added to the support either before or after incorporation of the nickel and rhenium salts. It should also be understood that metal catalysts, e.g., the nickel and rhenium, need not be added simultaneously with each other or with the promoter. They can be added in any sequence. Promoters can be added to the catalyst composition at desirable levels that are generally no higher than the metal, e.g., nickel, present in the catalyst composition on a weight percent basis. In some embodiments, a promoter/nickel ratio of 0 to about 0.5 can be useful. Further discussion of low metal loaded catalyst compositions on transitional alumina-based acidic mixed metal oxide supports may be found in U.S. Pat. No. 8,187,997, incorporated herein by reference.

Preferably, the catalyst and/or the supported catalyst composition are calcined prior to reduction. Generally, calcining can occur in air or an inert atmosphere such as one based upon nitrogen, argon, carbon dioxide, combinations of these, and the like. Calcining can occur at a variety of elevated temperatures, such as a temperature up to about 1000° C., preferably about 200° C. to about 800° C.

The catalyst material may be incorporated into the catalyst systems in a variety of ways. In some instances, a catalyst precursor is first provided on the support, and then the precursor can be converted into the catalyst itself afterward. Exemplary procedures are well known in the industry and include solution impregnation, precipitation, vapor deposition such as by PVD or CVD techniques, and the like.

The amount of catalyst used in the present invention is any amount which is effective in producing the desired product. For batch conditions, the quantity of catalyst may be in the range from about 0.1 to about 20 weight percent, preferably 1 to 15 weight percent, of catalyst per 100 parts by weight of reactant(s) employed. In a continuous process, a typical strategy might involve causing a flow of reactants to contact a bed of heterogeneous catalyst particles. In such a case, the space velocity (usually expressed in units of gmol/hr/kg catalyst) can be adjusted to balance factors such as production and selectivity.

Other amines may or may not be present in the mix. The total amount of reactants is 100 parts by weight. The heterogenous catalyst particles might include 5 part by weight of Ni and 1 part by weight of Re as metals for a total of 6 parts by weight of catalyst. In this case, the batch reactor would include 6 parts by weight of the catalyst per 100 parts by weight of the reactants. For purposes of the present invention, if the catalyst is present as a molecule such as an oxide or the like, only the weight of the active metal catalyst constituent is used to determine the weight percent.

The reaction mixture for transamination can be contacted with catalyst at any suitable temperature(s) that promotes the transamination reaction to produce the desired high molecular weight, branched, acyclic polyalkyleneamine. Typically, the temperature is maintained below about 350° C., preferably below 300° C. Preferred temperatures are in the range from about 130° C. to about 200° C. for transamination. Below the preferred temperature ranges, the conversion to polyalkyleneamines may be too slow to be practical for commercial scale production. Above the preferred temperature ranges, selectivity may be reduced to an undue degree, increasing the yield of by-products. In some instances, such by-products may have commercial value and be desirable as a consequence. In other instances, by-products constitute impurities as a practical matter.

Similarly, the reaction mixture for transamination can be contacted with catalyst at any suitable pressure(s) that promotes the reaction to produce the desired high molecular weight, branched, acyclic polyalkyleneamine. Preferably, the pressure is sufficient to maintain the reactor contents in a liquid state as the reaction proceeds. In many instances, the pressure will vary as the reaction proceeds. For instance, ammonia is a by-product of a typical transamination process. The production of ammonia causes the pressure generally to increase as the reaction proceeds in pressure sealed reactors. Ammonia and/or other pressure-increasing products can be removed from the reactor in order to keep the pressure below a desired threshold. Typically, the pressure is at least about 500 psi, preferably at least about 1000 psi, and preferably less than about 1500 psi. Within these guidelines, the pressure is typically in the range from about 100 psi to about 1500 psi, preferably about 200 psi to about 1500 psi, more preferably about 300 psi to about 1000 psi. For transamination, pressures in the range of about 400 psi to about 1000 psi are preferred.

In many embodiments, the amine mixture used as a starting reaction material for transamination will be in liquid form such that no additional solvent is needed. Indeed, in many instances it may be preferred to carry out the desired reaction in the absence of solvent. However, one or more solvents may be used if desired. A variety of solvents or combinations of solvents may be used. Desirably, the solvent is not unduly reactive with the amine reactant(s) or the resultant polyalkyleneamine product(s) and does not unduly decompose under the reaction conditions. Some examples of solvents that could be used include saturated hydrocarbons such as pentane, hexane, octane, nonane, decane, or the like; aromatic hydrocarbons such as toluene, benzene, xylene, or the like; ethers such as diethylether, tetrahydrofuran, or the like; combinations of these, and the like. Alcohols are desirably avoided, as many of these are capable of reacting with the amine reactants and/or products. If present, the amount of solvent used may vary over a wide range. In a typical instance, the solvent may constitute from about 5 to about 98 weight percent, desirably 10 to 80 weight percent, of the mixture. The reactant mixture for transamination optionally may, and preferably does, include hydrogen. When hydrogen is used, the level of hydrogen can be adjusted to favor the formation of the desired high molecular weight, branched, acyclic amine products while minimizing the amount of cyclic byproducts. Up to 100 mole percent, desirably about 0.1 to about 10 mole percent of hydrogen of as a part of the reaction mixture would be suitable.

The molecular weight of the amines produced by the methods of the present invention may be controlled by adding a terminator. A terminator is a non-polyalkyleneamine which will react with the polyalkyleneamine mixture to form a tertiary amine. So, for example, a terminator compound may be added during transamination to stop the reaction. Useful terminators include secondary amines (e.g., dimethylamine, diethylamine, etc.).

The present invention will now be further described with reference to the following illustrative examples.

Example 1

Catalyst

Precursor salts of nickel and rhenium were dissolved in 70-80° C. water to form an impregnation solution. The final volume of the impregnation solution was adjusted to equal the adsorption volume required for the number of times that the carrier was impregnated, and the quantities of the precursor salts were calculated to give a nominal composition of 6.8 and 1.8 wt. percent nickel and rhenium, respectively. The support was impregnated to incipient wetness by the addition of the appropriate amount of impregnation solution and gently agitated until all the liquid was adsorbed. The sample was then calcined in air at 340° C. When the support had cooled, additional impregnations were performed until all of the solution had been added. A calcination step at 340° C. was done after each impregnation. Prior to use, the catalyst compositions were reduced in hydrogen by ramping the temperature at 3° C./minute to 230° C., holding at this temperature for one hour, and then ramping at 3° C./minute to 340° C., and holding for 3 hours, or as otherwise specified in the Examples. The catalyst compositions were allowed to cool under hydrogen to ambient temperature, after which they were stabilized by adding a flowing stream of 1% oxygen in nitrogen until the exotherm ceased. At no time was the exotherm allowed to exceed about 70° C.

Reactor

The reaction was run in a 1 inch by 8 foot packed bed reactor. The reactor bed was made of 1 inch seamless stainless steel tubing (1 inch outside diameter, 0.095 in wall thickness). The length of the reactor tube was approximately 8 feet. It was incased in 1.5 inch diameter stainless steel tubing through which heat transfer fluid was pumped via a standard laboratory heating bath. This allowed for isothermal operation of the reactor tube. A multipoint thermocouple was placed inside the reactor bed for temperature monitoring. Temperature and pressure was monitored at various points in the reactor system. The amine feed material was pumped via a 500 ml syringe pump through a flow meter, a pre-heater, and into the bottom of the reactor. Just prior to the reactor tube inlet (bottom), the hydrogen gas was introduced to the amine feed stream. The reactor pressure was maintained at 800 psig using a back pressure regulator. At the reactor outlet, the pressure was let down to approximately 200-400 psi and the product mixture was sent to an intermediate tank. There was a sampling system that allows for a timed sample to be taken of the product stream. The sample time was dependent on the feed flow rate, but routinely samples were taken in the range of 15-30 minutes. The sampling system consisted of a stainless steel reservoir to collect the amine reaction mixture, followed by two small scrubbers, and a wet test meter. This allowed for quantification of the feed flow, ammonia generation, and hydrogen flow during sampling. The product mixture was analyzed by gas chromatography.

Analytical

Chemical structures of the product were confirmed by dissolving the reaction mixtures in acetonitrile and using flow injection analysis electrospray ionization mass spectrometry (FIA-ESI/MS) operating in the positive (PI) ion mode.

Feed

TAEA was obtained as a pale yellow viscous liquid from Pressure Chemical and was 89.5 wt. percent pure (other components identified include alcohol isomers 5.0%, diethylenetriamine (DETA) 0.5%, AEP 1.0%, N-methyl TAEA 2.0% and unidentified 2.0%). DAP was obtained from BASF.

Figure 1:
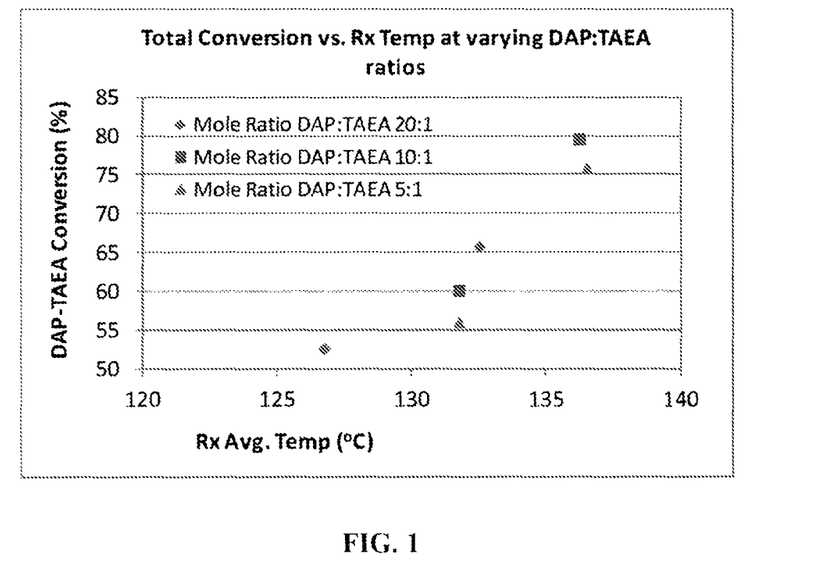
FIG. 1 is a graph showing total amine conversion (weight basis conversion for DAP and TAEA) as a function of temperature (° C.) at three different DAP to TAEA mole ratios.

Mole ratios of 20:1, 10:1, and 5:1 of DAP/TAEA were used as feed. FIG. 1 shows total amine conversion (weight basis conversion for DAP and TAEA) as a function of temperature (° C.) at three different DAP to TAEA mole ratios.

As expected, the higher the reactor temperature the higher the conversion. The feed mole ratio of DAP/TAEA had only a slight impact on overall amine conversion with the higher DAP/TAEA mole ratios giving the highest conversions at similar process conditions.

Figure 2:
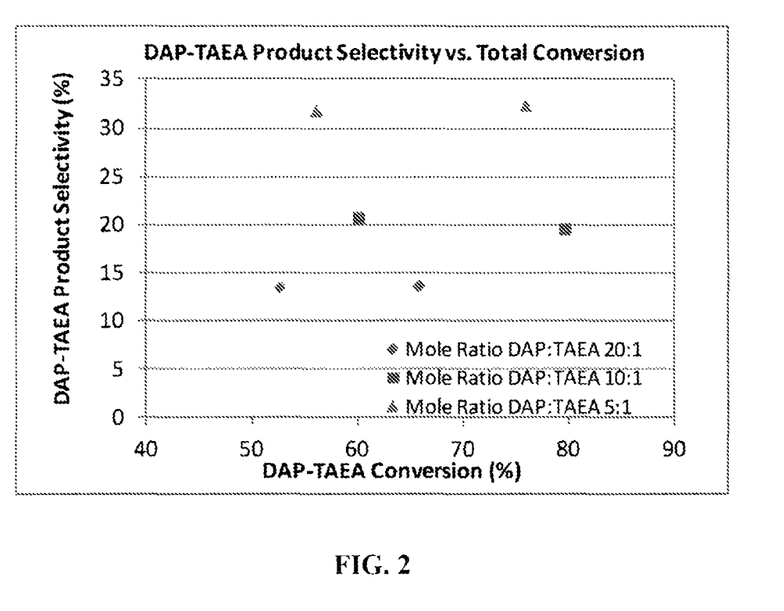
FIG. 2 is a graph showing DAP/TAEA products as a function of DAP and TAEA conversion at three different DAP/TAEA mole ratios.

FIG. 2 shows DAP/TAEA products as a function of DAP and TAEA conversion at three different DAP/TAEA mole ratios. The higher the TAEA in the DAP/TAEA mixed feed, the higher the selectivity to DAP/TAEA products (acyclic, branched polyalkyleneamines) and the lower the amount of DAP (linear non-branched) transamination products only.

Figure 3:
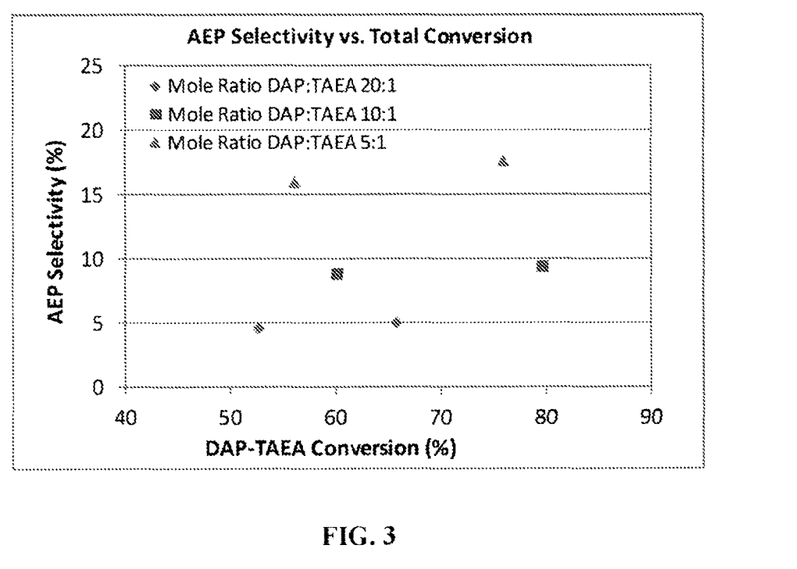
FIG. 3 is a graph showing weight percent AEP formed as a function of DAP/TAEA total conversion at three different DAP/TAEA mole ratios.

FIG. 3 shows weight percent AEP formed as a function of DAP/TAEA total conversion at three different DAP/TAEA mole ratios. The lower the DAP/TAEA ratio the higher the amount of AEP and other cyclic materials formed at a given DAP/TAEA conversion. This shows that when using TAEA as the second component it is important to have a first component free of any branching (e.g., DAP) for high reactivity and a high mole ratio of the first component compared to TAEA to minimize the ring closure of TAEA to AEP and keep the amount of cyclic polyalkyleneamines to less than 25 wt. percent of the predominately high molecular weight, branched, acyclic polyalkyleneamine congener products.

What is claimed:

1. A method of making a high molecular weight, branched, acyclic polyalkyleneamine-containing product comprising the steps of:
   (a) providing a reaction composition comprising a first linear polyalkyleneamine that has at least two non-tertiary amine groups separated by at least a ternary carbon atom spacing and at least one second polyalkyleneamine having the formula wherein x, y, and z are the same or different and are integers of from 1 to 10; a, b, c, d, e, and f are the same or different and are H or hydrocarbyl of from 1 to 10 carbon atoms, A, B, C, D, E, are the same or different and are H or hydrocarbyl of from 1 to 10 carbon atoms; provided that at least two of the amine groups are primary or secondary; and
   (b) subjecting the reaction composition to a transamination reaction in the presence of a hydrogenation/dehydrogenation catalyst to obtain the high molecular weight, branched, acyclic polyalkyleneamine-containing mixture.

2. The method of claim 1 wherein the first polyalkyleneamine has at least two non-tertiary amine groups separated from one another by a ternary or greater carbon group.

3. The method of claim 1, wherein the first polyalkyleneamine is selected from 1,3-diaminopropane (1,3-DAP), 1,3-pentanediamine; 1,3-butanediamine; 2,2-dimethyl-1,3-propanediamine; 2,2-diethyl-1,3-propanediamine; 1,3-diamino-2-phenylpropane; 2-(aminomethyl)-2-methyl-1,3-propanediamine; and combinations thereof.

4. The method of claim 1, wherein the second polyalkylene amine is tris(2-aminoethyl)amine (TAEA), tris(2-aminopropyl)amine, tris(3-aminopropyl)amine, and combinations thereof.

5. The method of claim 1, wherein the reaction composition comprises a mixture of 1,3-diaminopropane (DAP) and TAEA.

6. The method of claim 1, wherein the catalyst is a hydrogenation/dehydrogenation catalyst.

7. The method of claim 1, wherein the catalyst is supported on a substrate.

8. The method of claim 7, wherein the substrate comprises an acidic mixed metal oxide comprising a transitional alumina and a second metal oxide.

9. The method of claim 8, wherein the transitional alumina comprises delta alumina, and may optionally further comprise one or more of gamma, theta or alpha alumina.

10. The method of claim 8, wherein the second metal oxide is selected from silicon, lanthanum, magnesium, zirconium, boron, titanium, niobium, tungsten and cerium.

11. The method of claim 1, wherein the catalyst comprises:
   (a) a support portion comprising an acidic mixed metal oxide comprising a transitional alumina and a second metal oxide; and
   (b) a catalyst portion comprising nickel and rhenium, wherein:
   the second metal oxide has a weight percentage that is less than the weight percentage of alumina,
   (c) the catalyst portion is 25 weight percent or less of the catalyst composition,
   (d) the catalyst portion comprises nickel in an amount in the range of 2 to 20 weight percent, based upon total catalyst composition weight.

12. The method of claim 8, wherein the metal oxide is selected from one or more of magnesium, aluminum, titanium, vanadium, chromium, manganese, iron, cobalt, nickel, copper, zinc, gallium, boron, germanium, strontium, yttrium, zirconium, niobium, molybdenum, technetium, ruthenium, rhodium, palladium, silver, cadmium, indium, iron, tin, antimony, barium, lanthanum, hafnium, thallium, tungsten, rhenium, osmium, iridium, and platinum.

13. The method of claim 12, wherein the catalyst comprises a Ni/Re catalyst.

14. The method of claim 1, wherein the molar content of the first polyalkyleneamine comprises at least about 80% of the reaction mixture.

15. A mixture of predominately high molecular weight branched, acyclic polyalkyleneamine congener products obtained according to claim 11.

* * * * *